United States Patent
Grace et al.

(10) Patent No.: US 7,807,971 B2
(45) Date of Patent: Oct. 5, 2010

(54) MEASUREMENT OF MOISTURE IN COMPOSITE MATERIALS WITH NEAR-IR AND MID-IR SPECTROSCOPY

(75) Inventors: William B. Grace, Seattle, WA (US);
Gregory J. Werner, Puyallup, WA (US);
Paul H. Shelley, Lakewood, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/274,161

(22) Filed: Nov. 19, 2008

(65) Prior Publication Data

US 2010/0123079 A1    May 20, 2010

(51) Int. Cl.
*G01J 5/02* (2006.01)
(52) U.S. Cl. .................................. 250/339.09
(58) Field of Classification Search ................................ 250/339.01–339.15
See application file for complete search history.

(56) References Cited

U.S. PATENT DOCUMENTS

| | | | | |
|---|---|---|---|---|
| 5,104,488 | A * | 4/1992 | Chase | 162/198 |
| 5,107,118 | A * | 4/1992 | Murray et al. | 250/339.1 |
| 6,074,483 | A * | 6/2000 | Belotserkovsky et al. | 118/665 |
| 6,784,431 | B2 | 8/2004 | Shelley et al. | |
| 6,794,651 | B2 | 9/2004 | Shelley et al. | |
| 6,903,339 | B2 | 6/2005 | Shelley et al. | |
| 6,906,327 | B2 | 6/2005 | Shelley et al. | |
| 7,115,869 | B2 | 10/2006 | Shelley et al. | |
| 7,223,977 | B2 | 5/2007 | Shelley et al. | |
| 2002/0109093 | A1 * | 8/2002 | Kelley | 250/339.09 |
| 2002/0113212 | A1 * | 8/2002 | Meglen et al. | 250/339.05 |
| 2007/0131862 | A1 * | 6/2007 | Cowan et al. | 250/339.09 |

FOREIGN PATENT DOCUMENTS

WO    2009/064054    5/2009

OTHER PUBLICATIONS

Dao et al., "Accelerated ageing versus realistic ageing in a aerospace composite materials. IV. Hot/Wet ageing effects in a low temperature cure epoxy composite," 2007, Journal of Applied Polymer Science, vol. 106, pp. 4264-4276.*
Wichita State University, Bill Stevenson, Dept. of Chemistry, Methods for the Evaluation of Carbon Based Composite Surfaces for Subsequent Adhesive Bonding.

* cited by examiner

*Primary Examiner*—David P Porta
*Assistant Examiner*—Kiho Kim
(74) *Attorney, Agent, or Firm*—Tung & Associates (57) ABSTRACT

A method of determining moisture content of a composite material includes providing composite material standards with moisture content, collecting infrared spectra on the composite material standards, calibrating the infrared spectra to the moisture content, providing a composite material and predicting moisture content of the composite material based on the infrared spectra and the composite material standards.

21 Claims, 6 Drawing Sheets

MEASUREMENT OF MOISTURE IN COMPOSITE MATERIALS WITH NEAR-IR AND MID-IR SPECTROSCOPY

TECHNICAL FIELD OF THE INVENTION

The disclosure relates to methods for determining moisture content of composite materials. More particularly, the disclosure relates to a method for accurately assessing moisture content in a composite material using near-infrared and mid-infrared spectroscopy.

BACKGROUND OF THE INVENTION

Resin-fiber composite materials are utilized in a variety of applications including the aerospace industry, for example. Composite materials may absorb atmospheric moisture over time. The integrity of composite bonded repairs may be compromised as a result of absorbing moisture. Determining the quantity of moisture, which is present in a composite material, may facilitate determination of which steps are needed prior to bonding of the composite material.

Therefore, a method for accurately assessing moisture content in a composite material using field portable and user friendly near-infrared or mid-infrared spectroscopy is needed.

SUMMARY OF THE INVENTION

The present disclosure is generally directed to a method of determining moisture content of a composite material. An illustrative embodiment of the method includes obtaining a calibration for moisture content in a series of composite material samples using the IR spectra of infrared energy reflected from the composite material samples, providing a series of moisture standards in appropriate composite materials that have increasing steps of moisture content, performing the multivariate calibration of IR spectra to moisture content with appropriate pre-processing of the IR spectra as needed and then using that calibration to predict the moisture content in the same type of composite materials where the moisture content is not known.

The disclosure is further generally directed to a method of determining a physical property of a composite material (for example weight percent moisture and/or G1c value for bond strength by the double cantilever beam bond toughness test). An illustrative embodiment of the method includes obtaining a value for a physical property of a composite material sample as a function of moisture content of the composite material sample, obtaining a calibration between moisture content of the composite material sample and a spectrum of infrared energy reflected from the composite material sample, obtaining a calibration between the spectrum of infrared energy reflected from the composite material sample and the value for a physical property of the composite material sample, and using the calibration to predict the physical properties of composite materials in question from the IR spectra of those materials in question.

BRIEF DESCRIPTION OF THE ILLUSTRATIONS

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the invention and are not intended to limit the scope of the invention, which is defined by the claims. Furthermore, there is no intention to be bound by any expressed or implied theory presented in the preceding technical field, background, brief summary or the following detailed description.

Figure 1:
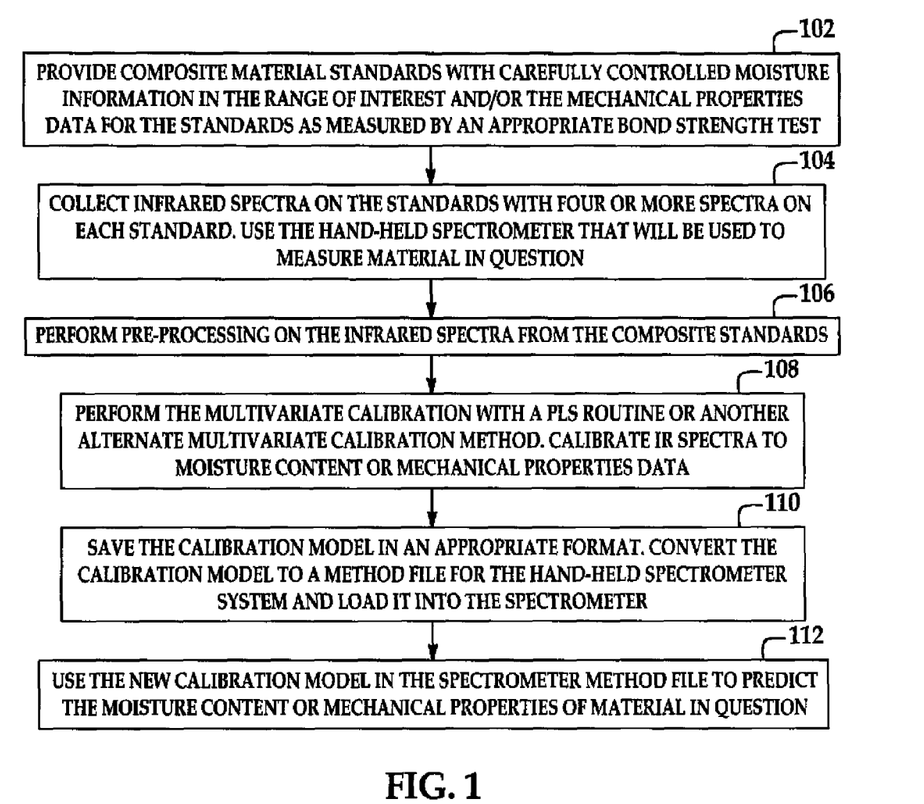
FIG. 1 is a flow diagram which illustrates an illustrative method of performing a calibration between spectra of near-infrared and mid-infrared energy and moisture content or mechanical properties of composite material samples exposed to various quantities of moisture over various time periods.

Referring initially to FIG. 1, a flow diagram 100 which illustrates an illustrative method of obtaining a calibration between spectra of infrared energy and moisture content of composite material samples exposed to various quantities of moisture over various time periods is shown. In block 102, composite material samples are provided with controlled moisture content information over the range of interest for good to poor bond strength results. The composite material samples may be 2-inch composite material squares, for example and without limitation. In block 104, the composite material sample series is measured with the hand-held spectrometer that will be used to measure material in question later. This can be a spectra with the infrared spectra range only; such as near infrared or a mid infrared device for various materials and situations.

In block 106, the infrared data is preprocessed with an appropriate algorithm to provide the best data for the calibration of spectral data to moisture content. In block 108, the multivariate calibration is preformed. This of often a Partial Least Squares (PLS) regression of moisture content data to the infrared spectra. In block 110, the calibration model is saved in an appropriate format and is loaded into the hand held device that will be used to make measurements of material in question. In block 112 the calibration model in the spectrometer is used to predict moisture content on materials in question using new spectra on those materials.

Figure 2:
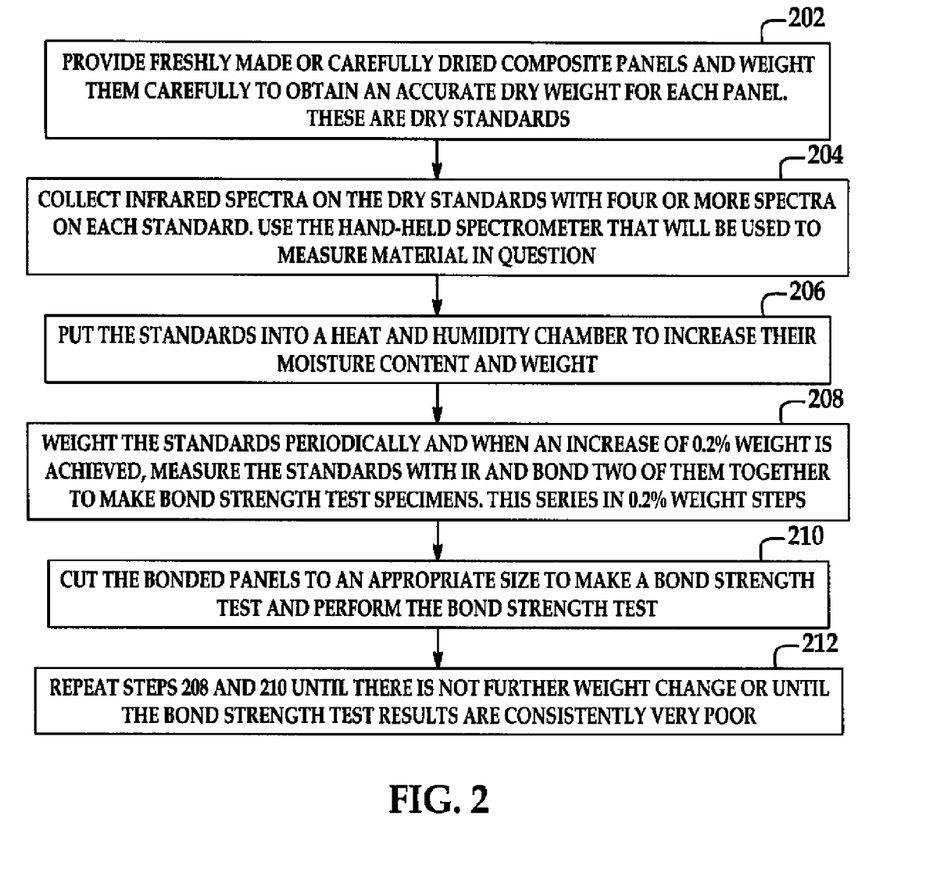
FIG. 2 is a flow diagram which illustrates an illustrative method for making a series of panels with increasing moisture content and obtaining the bond strength properties with increasing moisture content.

Referring next to FIG. 2, a flow diagram 200 which illustrates an illustrative method of making moisture content standards for the multivariate calibration and prediction method of FIG. 1. In block 202, a set of dried composite panels is provided and carefully weighted. In block 204, the dry standards are measured with a hand-held infrared spectrometer in order to obtain the dry material spectra for all the dry standards. In other applications, the surface of the composite material may be irradiated with near-spectrum or mid-spectrum infrared energy. In some applications, the infrared spectra may be obtained using a hand-held spectrometer system such as that which is available from the Polychromix corp. or A2 Technologies, for example and without limitation.

In block 206, the dry standards are put into a heat and humidity chamber to increase their moisture content. In block 208, the standards are weighed periodically until an increase of about 0.2%. With each increase of 0.2% weight a pair of standards are measured with a hand-held spectrometer and then the pair are bonded together in order to test the bond strength at the increased moisture content level. In block 210, the bonded panels are cut to an appropriate size for the bond strength test and the bond strength test is performed. In block 212 steps 208 and 210 are repeated until there is no further weight change or until the bond strength test results are consistently poor.

Figure 3:
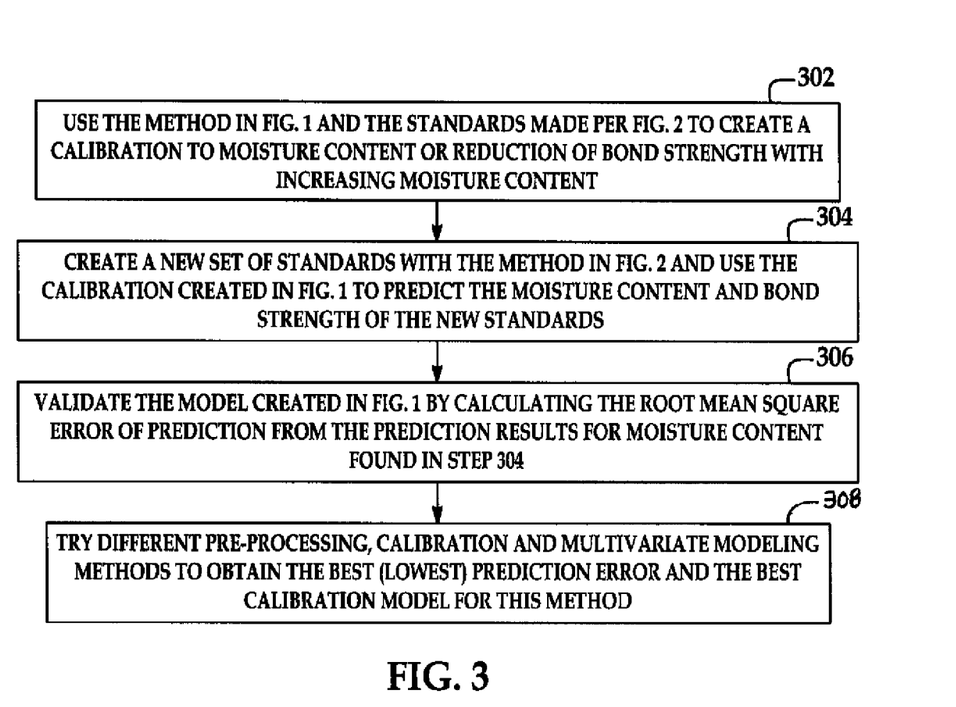
FIG. 3 is a flow diagram, which illustrates a way to validate the calibration model for moisture measurement in composite materials.

Referring next to FIG. 3, a flow diagram 300, which illustrates an illustrative method for validating the multivariate model that was made for moisture content measurement is shown. In block 302, the methods shown in FIG. 1 and the standards made in FIG. 2 are used to make an appropriate model of moisture content or reduction of bond strength with increasing moisture content versus changes in the infrared' spectra. In block 304, a new set of standards is created using the same method that was illustrated in FIG. 2 and this new set panels is predicted for moisture content and bond strength with the method created in FIG. 1. In block 306, the multivariate model is validated by calculating the root mean square error of prediction from the prediction results in step 304 and the actual moisture content by weight percent increase. In block 308 the model is optimized by using various data preprocessing and calibration methods to obtain the lowest possible prediction error in this validation step.

Figure 4:
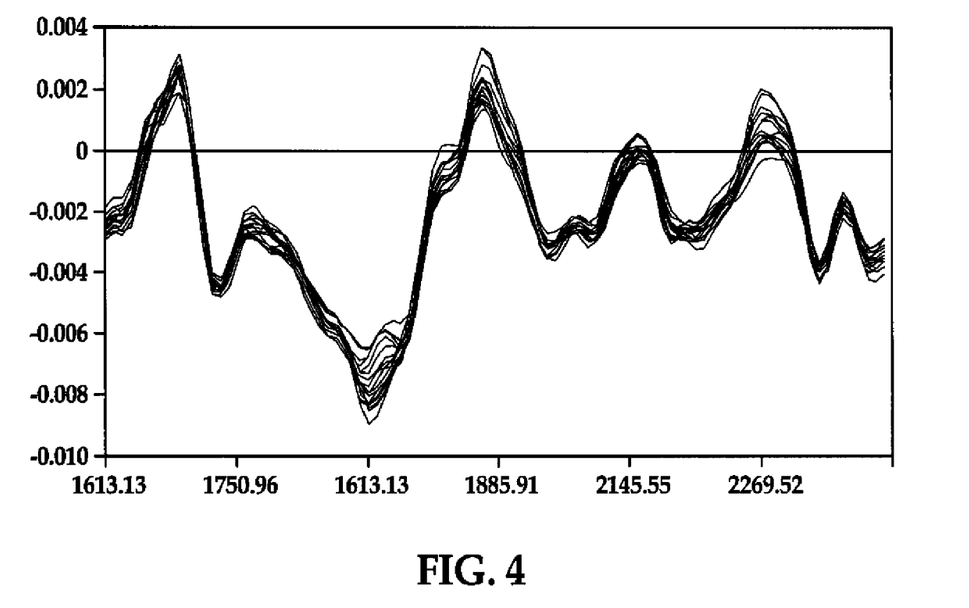
FIG. 4 is a graph, which illustrates near infrared spectra on 100 scans of moist and dry composite material tape using first derivative data with 5 smoothing points.
Figure 5:
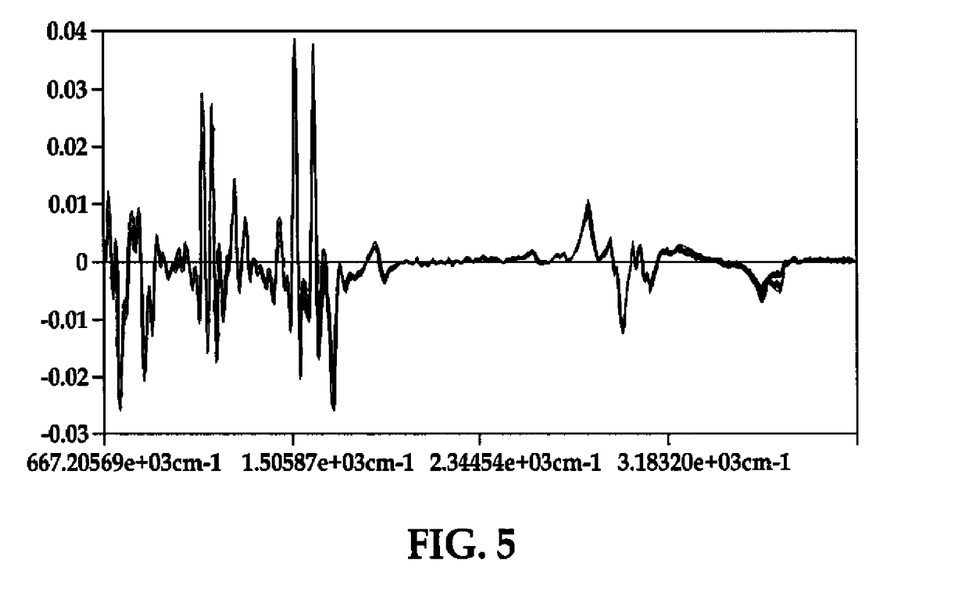
FIG. 5 is a graph, which illustrates mid infrared spectra of an average of 128 scans of moist and dry composite material tape using first derivative data with 7 smoothing points.
Figure 6:
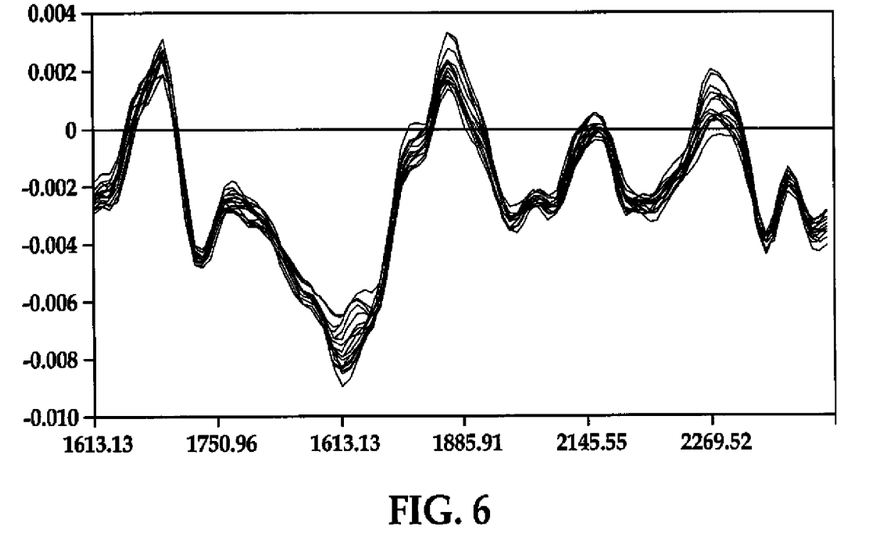
FIG. 6 is a graph, which illustrates baseline offset corrected mid infrared data on 128 averaged scans of moist and dry composite material tape.
Figure 7:
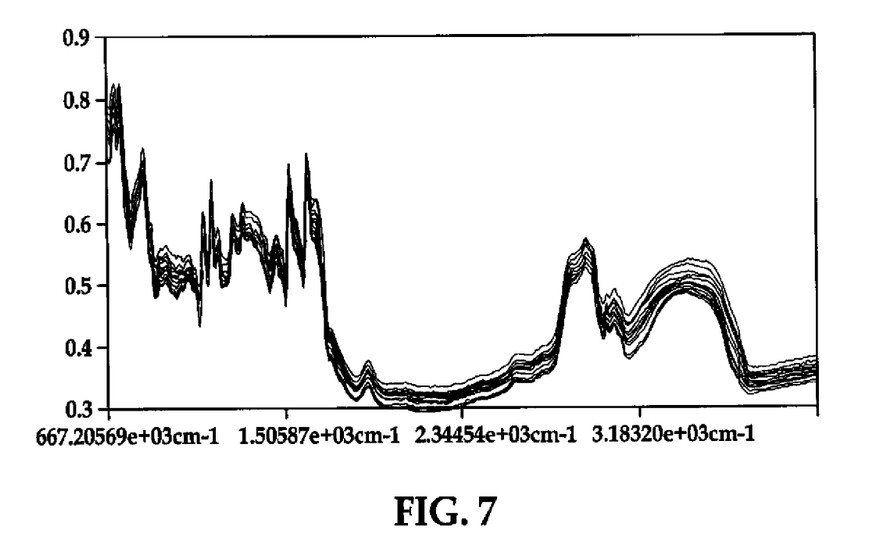
FIG. 7 is a graph, which illustrates raw mid infrared data on 128 averaged scans of moist and dry composite material tape.

Referring next to FIGS. 4-7, graphs which illustrate infrared spectra obtained from composite materials having various degrees of moisture content are shown. In FIG. 4, a graph, which illustrates near infrared spectra on 100 scans of moist and dry composite material tape using first derivative data with 5 smoothing points is shown. In FIG. 5, a graph, which illustrates mid infrared spectra of an average of 128 scans of moist and dry composite material tape using first derivative data with 7 smoothing points is shown. In FIG. 6, a graph, which illustrates baseline offset corrected mid-TR data on 128 averaged scans of moist and dry composite material tape is shown. In FIG. 7, a graph, which illustrates raw mid-IR data on 128 averaged scans of moist and dry composite material tape is shown.

Figure 8:
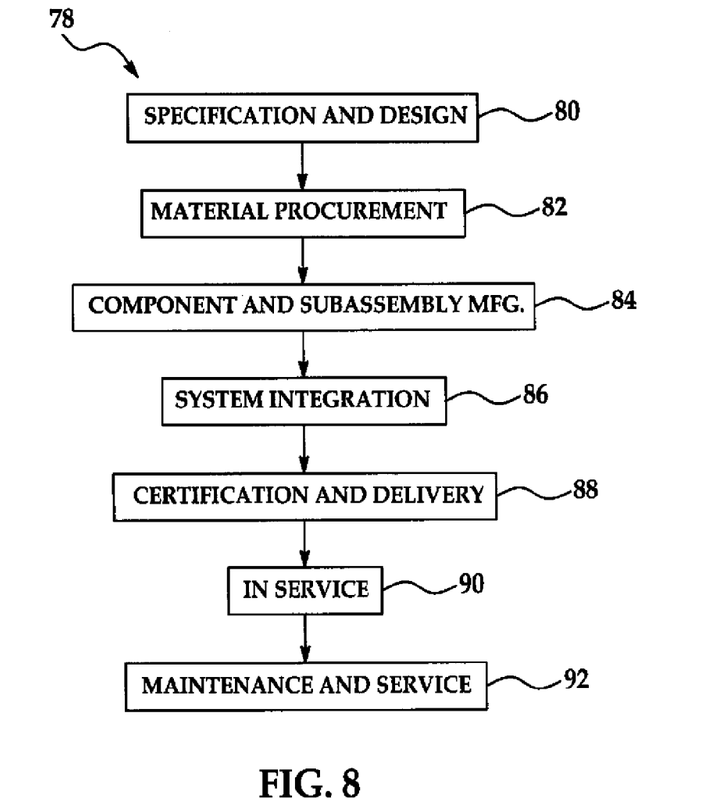
FIG. 8 is a flow diagram of an aircraft production and service methodology.
Figure 9:
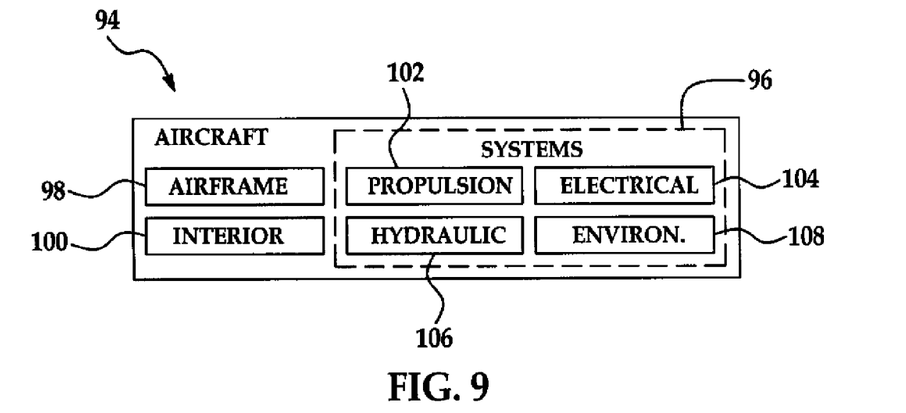
FIG. 9 is a block diagram of an aircraft.

Referring next to FIGS. 8 and 9, embodiments of the disclosure may be used in the context of an aircraft manufacturing and service method 78 as shown in FIG. 8 and an aircraft 94 as shown in FIG. 9. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 9, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining moisture content of a resin-fiber composite material, comprising:
    providing solid resin-fiber composite material standards with moisture content;
    collecting at least one of broad-band near and mid-spectrum infrared spectra of infrared energy reflected from said resin-fiber composite material standards, said spectra are within the infrared spectra range only;
    calibrating said infrared spectra to said moisture content;
    providing a solid resin-fiber composite material;
    collecting said infrared spectra from said composite material;
    predicting moisture content of said composite material based on said infrared spectra and said composite material standards; and,
    quantitatively predicting a mechanical property of said composite material based on said predicted value of said moisture content of said composite material.

2. The method of claim 1 wherein said calibrating said infrared spectra to said moisture content with infrared energy comprises calibrating said infrared spectra to said moisture content with near-spectrum infrared energy.

3. The method of claim 1 wherein said calibrating said infrared spectra to said moisture content with infrared energy comprises calibrating said infrared spectra to said moisture content with mid-spectrum infrared energy.

4. The method of claim 1 wherein said calibrating said infrared spectra to said moisture content comprises calibrating said infrared spectra to said moisture content using a hand-held spectrometer.

5. The method of claim 1 further comprising performing pre-processing on said infrared spectra.

6. The method of claim 1 wherein said calibrating said infrared spectra to said moisture content comprises calibrating said infrared spectra to said moisture content using a Partial Least Squares (PLS) regression.

7. The method of claim 1 further comprising converting calibration data resulting from said calibrating said infrared spectra to said moisture content to a method file for a hand-held spectrometer.

8. The method of claim 1, wherein said mechanical property comprises a bond strength of said fiber-resin composite material to a second fiber-resin composite material.

9. A method of predicting a mechanical property of a resin-fiber composite material based on moisture content, comprising:
obtaining a calibration of moisture content in solid resin-fiber composite material standards with spectra comprising at least one of broad-band near and mid-spectrum spectra of infrared energy reflected from said composite material standards, said spectra are within the infrared spectra range only;
correlating a mechanical property of said composite material standards with said spectra of infrared energy and said moisture content in said composite material standards;
creating a model of changes in moisture content of said composite material standards versus changes in said spectra of infrared energy reflected from said composite material standards;
providing a solid resin-fiber composite material having a surface;
obtaining said spectra of infrared energy reflected from said surface of said composite material using a hand-held spectrometer; and
quantitatively predicting said mechanical property of said composite material based on a predicted value of said moisture content of said composite material using said model.

10. The method of claim 9 wherein said obtaining spectra of infrared energy reflected from said surface of said composite material comprises obtaining spectra of infrared energy reflected from said surface of said composite material with near-spectrum infrared energy.

11. The method of claim 9 wherein said obtaining spectra of infrared energy reflected from said surface of said composite material comprises obtaining spectra of infrared energy reflected from said surface of said composite material with mid-spectrum infrared energy.

12. The method of claim 9 wherein said obtaining spectra of infrared energy reflected from said surface of said composite material comprises obtaining spectra of infrared energy reflected from said surface of said composite material using a hand-held spectrometer.

13. The method of claim 9 wherein said obtaining a calibration of moisture content in composite material standards with spectra of infrared energy reflected from said composite material standards comprises collecting at least four spectra of infrared energy reflected from each composite material standard, performing pre-processing on said spectra and performing multivariate calibration on said spectra.

14. The method of claim 9, wherein said mechanical property comprises a bond strength of said fiber-resin composite material to a second fiber-resin composite material.

15. A method of determining a mechanical property of a resin-fiber composite material based on moisture content, comprising:
obtaining a calibration of moisture content in resin-fiber composite material standards with at least one of broad-band near and mid-spectrum spectra of infrared energy reflected from said composite material standards, said spectra not are within the infrared spectra range only, by:
providing a plurality of said composite material standards with controlled moisture content;
collecting said infrared spectra on said composite material standards; and calibrating said infrared spectra to moisture content of said composite material standards;
correlating said moisture content in said composite material standards with said mechanical property of said composite material standards by;
providing a first set of resin-fiber composite material standards;
obtaining said infrared spectra of said first set of composite material standards; and determining and correlating said mechanical property of said first set of composite material standards with said infrared spectra and increasing moisture content of said first set of composite material standards;
creating a model of changes in moisture content and changes in said mechanical property of said first set of composite material standards versus changes in said infrared spectra of said first set of composite material standards;
providing a second set of resin-fiber composite material standards with varying moisture content;
obtaining said infrared energy spectra of said second set of composite material standards; and quantitatively predicting moisture content and said mechanical property of said second set of composite material standards using said model.

16. The method of claim 15 wherein said obtaining infrared spectra of said first set of composite material standards comprises obtaining infrared spectra of said first set of composite material standards with near-spectrum infrared energy.

17. The method of claim 15 wherein said obtaining infrared spectra of said first set of composite material standards comprises obtaining infrared spectra of said first set of composite material standards with mid-spectrum infrared energy.

18. The method of claim 15 wherein said obtaining infrared spectra of said first set of composite material standards comprises obtaining infrared spectra of said first set of composite material standards using a hand-held spectrometer.

19. The method of claim 15 wherein said calibrating said infrared spectra to moisture content of said composite material standards comprises performing multivariate calibration using a Partial Least Squares (PLS) regression.

20. The method of claim 15, wherein said mechanical property comprises a bond strength of said fiber-resin composite material to a second fiber-resin composite material.

21. A method of determining bond strength of a first resin-fiber composite material to a second resin-fiber composite material based on moisture content, comprising:
obtaining a calibration of moisture content in resin-fiber composite material standards with at least one of broad-band near and mid-spectrum spectra of infrared energy reflected from said composite material standards, said spectra are within the infrared spectra range only, by:
providing a plurality of resin-fiber composite material standards with controlled moisture content;
collecting infrared spectra on said composite material standards; and
calibrating said infrared spectra to moisture content of said composite material standards;
correlating said moisture content in said composite material standards with bond strength of said composite material standards by providing a first set of resin-fiber composite material standards;

obtaining infrared spectra of said first set of composite material standards; and determining and correlating bond strength of said first set of composite material standards with said ,infrared spectra and increasing moisture content of said first set of composite material standards;

creating a model of changes in moisture content and changes in said mechanical property of said first set of composite material standards versus changes in said infrared spectra of said first set of composite material standards;

providing a second set of resin-fiber composite material standards with varying moisture content;

obtaining said infrared energy spectra of said second set of composite material standards;

quantitatively predicting moisture content and said bond strength of said second set of composite material standards using said model; and validating said model by calculating a root mean square of prediction from prediction results of said predicting moisture content and said bond strength of said second set of composite material standards using said model.

* * * * *